United States Patent
Limanskiy

(10) Patent No.: US 11,384,974 B2
(45) Date of Patent: Jul. 12, 2022

(54) REFRIGERATOR SYSTEM

(71) Applicant: WHIRLPOOL CORPORATION, Benton Harbor, MI (US)

(72) Inventor: Semen Viktorovich Limanskiy, Lipetsk (RU)

(73) Assignee: WHIRLPOOL CORPORATION, Benton Harbor, MI (US)

( * ) Notice: Subject to any disclaimer, the term of this patent is extended or adjusted under 35 U.S.C. 154(b) by 0 days.

(21) Appl. No.: 17/120,915

(22) Filed: Dec. 14, 2020

(65) Prior Publication Data
US 2022/0187005 A1 Jun. 16, 2022

(51) Int. Cl.
F25D 17/04 (2006.01)
F25D 27/00 (2006.01)

(52) U.S. Cl.
CPC ........... *F25D 17/042* (2013.01); *F25D 27/00* (2013.01); *F25D 2317/0416* (2013.01); *F25D 2317/0417* (2013.01); *F25D 2400/22* (2013.01)

(58) Field of Classification Search
CPC ........... F25D 2317/04; F25D 2317/041; F25D 2317/0413; F25D 2317/04131; F25D 2317/0416; F25D 2317/0417; F25D 2327/00; F25D 2400/22; F25D 17/00; F25D 17/02; F25D 17/005; F25D 17/04; F25D 17/042; F25D 23/065; F25D 23/067; F25D 27/00; F25D 27/005
See application file for complete search history.

(56) References Cited

U.S. PATENT DOCUMENTS

| 4,955,208 A * | 9/1990 | Kawashima | A61L 9/20 62/264 |
| 5,230,220 A * | 7/1993 | Kang | A61L 9/015 62/264 |
| 6,967,008 B1 * | 11/2005 | Barnes | A01M 29/12 422/186.07 |
| 10,139,150 B2 | 11/2018 | De Cavalcanti et al. | |
| 2012/0036879 A1 | 2/2012 | Candeo et al. | |
| 2020/0124339 A1 | 4/2020 | Cheng et al. | |

FOREIGN PATENT DOCUMENTS

| AU | 2018102157 A4 | 3/2020 |
| CN | 2401534 Y | 10/2000 |
| CN | 102365514 B | 4/2015 |
| CN | 205641742 U | 10/2016 |

(Continued)

*Primary Examiner* — Andrew M Roersma
(74) *Attorney, Agent, or Firm* — Brooks Kushman P.C.

(57) ABSTRACT

A refrigerator includes a rear wall, a first strap, a second strap, an insulative member, a housing, an ozone generator, a ventilation panel, and a light. The first strap and the second strap fix the insulative member to the rear wall. The housing is disposed in the ventilation panel. A frontside of the housing has a recessed portion that defines a receptacle on a backside of the wall, a trough on the frontside of the wall, and a first number of vents. The first number of vents establish fluid communication between the receptacle and the trough. The ozone generator is disposed in the receptacle. The light is fixed to the housing. The light includes a cover that overlaps at least a portion of the trough and defines a second number of vents that are in fluid communication with the trough.

15 Claims, 8 Drawing Sheets

(56) References Cited

FOREIGN PATENT DOCUMENTS

| | | | | |
|---|---|---|---|---|
| CN | 107036369 | A | 8/2017 | |
| CN | 107782041 | A | 3/2018 | |
| CN | 110895072 | A | 3/2020 | |
| CN | 211214574 | U | 8/2020 | |
| EP | 0282301 | A2 | 9/1988 | |
| EP | 2401563 | B1 | 10/2016 | |
| EP | 3343155 | A1 | 7/2018 | |
| EP | 3643997 | A1 | 4/2020 | |
| ES | 2073960 | A2 * | 8/1995 | ........... F25D 17/042 |
| JP | S6449874 | A | 2/1989 | |
| JP | H-01266483 | A * | 10/1989 | ............. F25D 27/00 |
| JP | H03101810 | A | 4/1991 | |
| JP | H04306478 | A | 10/1992 | |
| JP | 3338218 | B2 | 10/2002 | |
| JP | 2005106298 | A | 4/2005 | |
| JP | 2020524252 | A | 8/2020 | |
| KR | 890008636 | Y | 6/1986 | |
| KR | 20120007500 | A | 1/2012 | |
| KR | 101923458 | B1 | 11/2018 | |
| KR | 20190028037 | A | 3/2019 | |
| WO | 2010099464 | A2 | 9/2010 | |
| WO | 2010099464 | A3 | 9/2010 | |
| WO | 2018233479 | A1 | 12/2018 | |

* cited by examiner

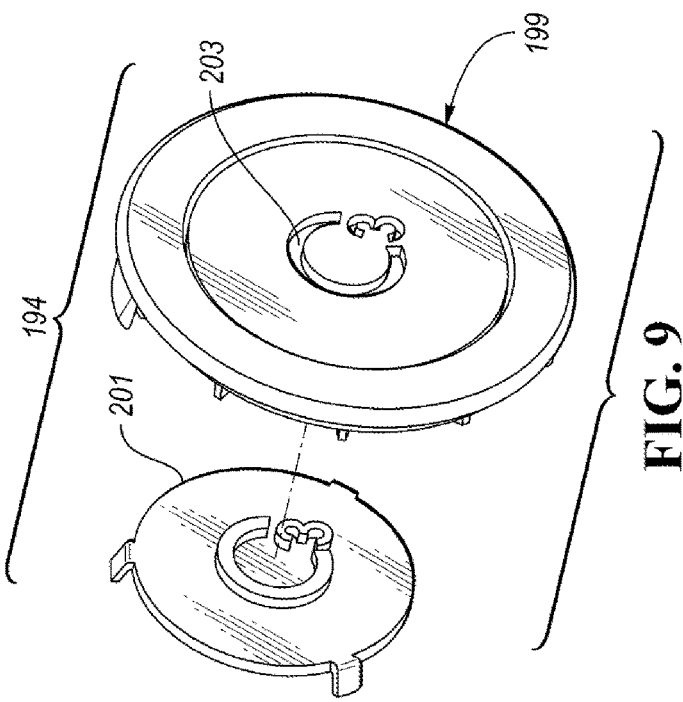
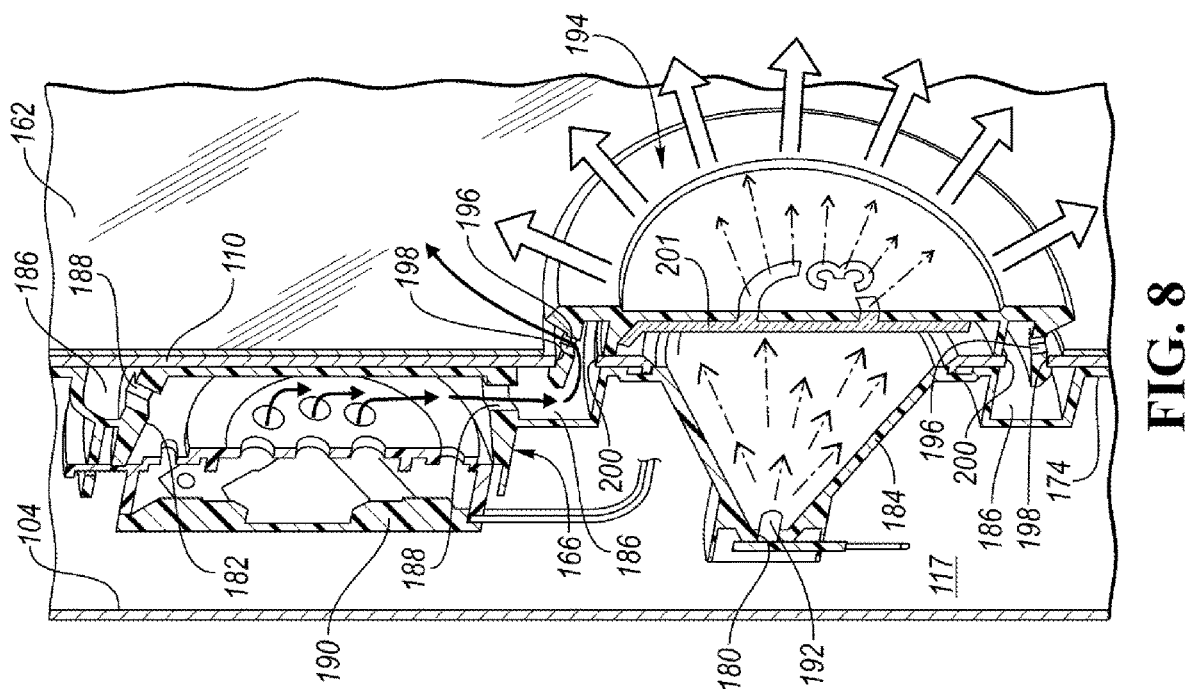

REFRIGERATOR SYSTEM

The present disclosure relates to an appliance such as a refrigerator.

BACKGROUND

In order to keep food fresh, a low temperature must be maintained within a refrigerator to reduce the reproduction rate of harmful bacteria. Refrigerators circulate refrigerant and change the refrigerant from a liquid state to a gas state by an evaporation process. A compressor increases the pressure, and in turn, the temperature of the gas refrigerant. This heated gas is then cooled by ambient air received from one or more vents often disposed on a rear portion of the refrigerator.

SUMMARY

A refrigerator includes a rear wall, a first strap, a second strap, an insulative member, a housing, an ozone generator, a first ventilation panel, and a light. The first strap and the second strap are each fixed to the rear wall. The insulative member defines a first aperture and extends between the first strap and the second strap. The housing is disposed in the first aperture. The housing includes a top end, a bottom end, and a wall extending therebetween. A frontside of the wall has a recessed portion that defines a receptacle on a backside of the wall, a trough on the frontside of the wall, and a first number of vents. The first number of vents establish fluid communication between the receptacle and the trough. The ozone generator is disposed in the receptacle. The first ventilation panel is disposed over the trough and at least a portion of the frontside of the wall. The first ventilation panel is fixed to the insulative member and defines at least one slot. The at least one slot is in fluid communication with the trough and is configured to receive ozonated fluid from the ozone generator via the trough, first number of vents, and receptacle. The light is fixed to the wall and is disposed between the bottom end and the ozone generator. The light includes a cover that overlaps at least a portion of the trough and defines a second number of vents. The second number of vents are in fluid communication with the at least one slot and are configured to vent the ozonated fluid from the at least one slot to an interior portion of the refrigerator.

A fixation system for use in a refrigerator includes a first strap and a second strap. The refrigerator has an insulative member and a ventilation panel defining a number of vents. The second strap is spaced apart from the first strap. The first strap and the second strap are collectively configured to receive the insulative member. The first strap includes a main body having a rear side and a front side opposing the rear side. The rear side is configured to lie against a rear wall of the refrigerator and defines a first aperture configured to receive a first fastener to fix the main body to the rear wall of the refrigerator. The front side defines a second aperture configured to receive a second fastener to fix the ventilation panel to the main body.

An ozone generator assembly for use in a refrigerator includes a housing, an ozone generator, and a light. The housing includes a top end, a bottom end, and a wall extending therebetween. The wall includes an interior-facing surface defining a first aperture and a receptacle disposed above the first aperture. The wall includes an exterior-facing surface that is opposite the interior-facing surface. The exterior-facing surface defines a trough that extends inward from the exterior-facing surface and extends circumferentially about at least a portion of the receptacle. The housing defines a first number of vents that establish fluid communication between the receptacle and the trough. The ozone generator is at least partially disposed in the receptacle and is configured to supply ozonated fluid to the trough via the receptacle and the first number of vents. The light is secured to the housing and disposed in the first aperture. The light includes a cover disposed over the exterior-facing surface of the wall. The cover defines a second number of vents configured to receive the ozonated fluid from the first number of vents via the trough and provide the ozonated fluid to an interior portion of the refrigerator.

BRIEF DESCRIPTION OF THE DRAWINGS

FIG. 8 is a partial isometric cross-sectional view taken along line D-D in FIG. 1; and FIG. 9 is an exploded isometric view of a light cover for the ozone generator assembly.

DETAILED DESCRIPTION

Figure 2:
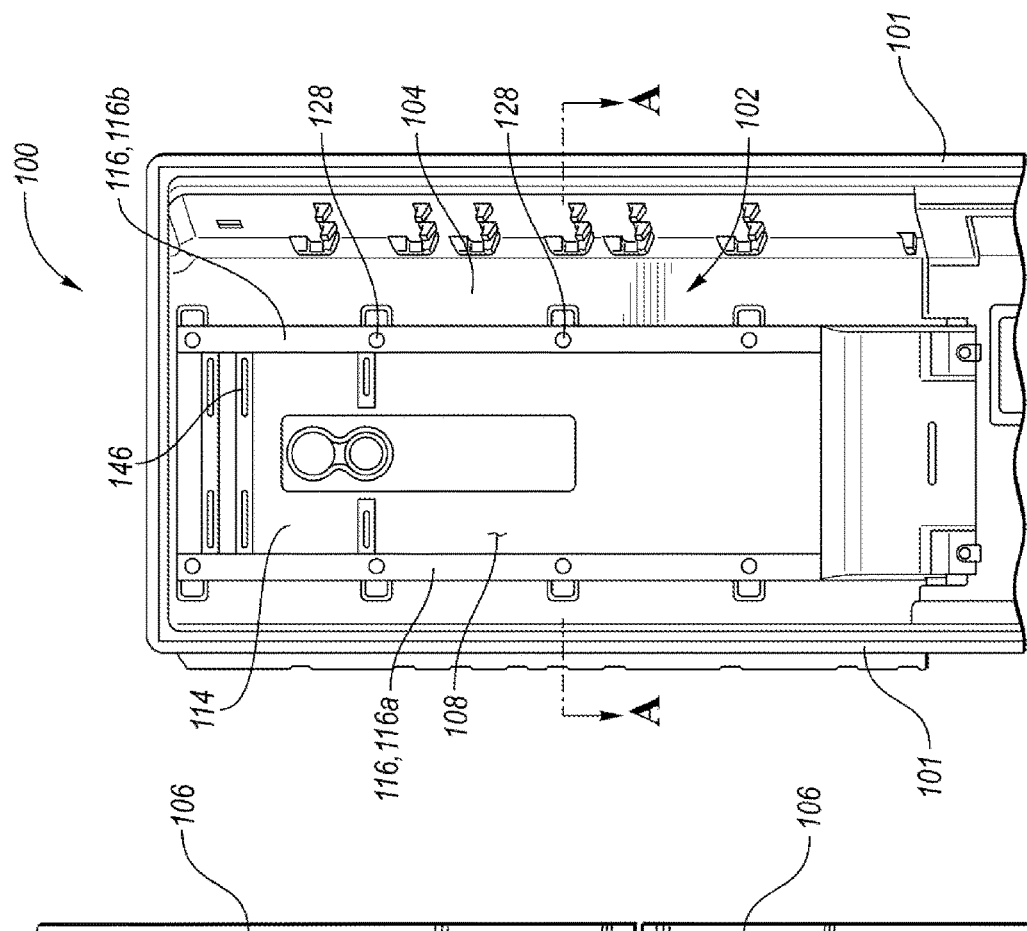
FIG. 2 is a front view of a portion of the refrigerator with the shelving and storage bins removed.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As used in the specification and the appended claims, the singular form "a," "an," and "the" comprise plural referents unless the context clearly indicates otherwise. For example, reference to a component in the singular is intended to comprise a plurality of components.

The term "substantially" or "about" may be used herein to describe disclosed or claimed embodiments. The term "substantially" or "about" may modify a value or relative characteristic disclosed or claimed in the present disclosure. In such instances, "substantially" or "about" may signify that the value or relative characteristic it modifies is within ±0%, 0.1%, 0.5%, 1%, 2%, 3%, 4%, 5% or 10% of the value or relative characteristic.

Spatially relative terms, such as "inner," "outer," "beneath," "below," "lower," "above," "upper," and the like, may be used for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Although the terms first, second, third, etc. may be used to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Refrigerators heat refrigerant by a compressor and then cool the refrigerant in a condenser, that may be mounted to a rear wall of the refrigerator. The rear wall of the refrigerator may include a number of vents that may draw in ambient air to cool the condenser and refrigerant contained therein. The rear wall within the refrigerator may include a ventilation panel that defines a number of vents configured to vent air from the interior of the refrigerator to the exterior of the refrigerator. Generally, the ventilation panel may be attached to an interior surface of the rear wall of the refrigerator by a number of fasteners such as screws. Fastening the panel by threading each of the screws may be time intensive. Moreover, the fasteners must be covered by a plug or cover to conceal the fastener and provide a more aesthetic appearance.

An insulative member may be disposed between the ventilation panel and the rear wall of the refrigerator. The insulative member may be inserted into a cavity or recessed portion defined by the rear wall of the refrigerator. As an example, the insulative member may be manually assembled to the rear wall by an operator. The operator subsequently fastens the ventilation panel to the rear wall of the refrigerator. In other words, the ventilation panel retains the insulative member between the ventilation panel and the rear wall. Because the insulative member is not directly fixed to the rear wall of the refrigerator, there may be gaps between the insulative member and the rear wall of the refrigerator. These gaps may lead to thermal inefficiencies.

Referring generally to the Figures, a refrigerator 100 according to one or more embodiments is provided. The refrigerator 100 may include several outer walls 101 that define an internal chamber 102. One of the outer walls may be a rear wall 104. One or more doors 106 may be pivotally attached to one of the outer walls 101. The rear wall 104 may include an interior surface 108 that is visible when one or more of the doors 106 is open. A ventilation panel 110 or flow panel may be disposed on the interior surface 108 of the rear wall 104. The ventilation panel 110 may include a number of apertures such as slots or vents 112 that may be configured to vent air (or facilitate an exchange of air) from the internal chamber 102 to an exterior of the refrigerator 100.

An insulative member 114 and a number of straps 116 may lie against a recessed portion 118 of the rear wall 104. As an example, the insulative member 114 may extend between a first strap 116a and a second strap 116b that may each be disposed within the recessed portion 118 of the rear wall 104. The ventilation panel 110 may be fixed to one or more of the straps 116 so that the insulative member 114 and straps 116 are sandwiched between the rear wall 104 and the ventilation panel 110. The insulative member 114 and the rear wall 104 may operate to form a duct 117 along a rear portion of the refrigerator (e.g., rear wall 104) to channel air from the internal chamber 102 to an exterior of the refrigerator 100. The slots or vents 112 of the ventilation panel 110 may be configured to vent air from the internal chamber 102 to the exterior of the refrigerator 100 via the duct 117.

In one or more embodiments, the insulative member 114 may be fixed to the first strap 116a and the second strap 116b by a press-fit condition. Alternatively, the insulative member 114 may be adhered to the straps 116 by an adhesive. As another example, one or more fasteners (not illustrated) may fix the insulative member 114 to the straps 116.

One or more of the straps 116 include a main body 120 provided with a rear side 124 and a front side 122 that opposes or is opposite to the rear side 124. In one or more embodiments, a sidewall 138 may extend between the rear side 124 and the front side 122. A flange 140 may extend from the sidewall 138 and engage portions of the insulative member 114.

The rear side 124 may define one or more first apertures 126 that each may be configured to receive a first fastener 130. The first fastener 130 may comprise one or more first fasteners 130. The one or more first apertures 126 each may be a portion of counterbore hole or may refer to a counterbore hole as a whole. The one or more first fasteners 130 may be configured to fix the straps 116 (or more specifically the main bodies 120 of the straps 116) to the rear wall 104. As an example, the one or more first fasteners 130 may be screws that are configured to thread into the rear wall 104 (or a more specifically into plugs 131 that are secured within recesses in the rear wall 104) to clamp the straps 116 and the insulative member 114 against the rear wall 104. In other words, the one or more first fasteners 130 may bias the strap 116 and insulative member 114 towards the rear wall 104 so that portions of the insulative member 114, such as protrusions 132, lie against the rear wall 104. The protrusions 132 may be configured to compress or deform as the first fastener 130 is tightened.

The front side 122 of the strap 116 may define one or more second apertures 128 that each may be configured to receive a second fastener 134. The second fastener 134 may comprise one or more second fasteners 134. The one or more second fasteners 134 may be configured to secure or fix the ventilation panel 110 to the straps 116. The one or more second apertures 128 each may be a portion of countersunk hole or may refer to a countersunk hole as a whole. The one or more second fasteners 134 may be a press-fit fasteners, such that pressing the one or more second fasteners 134 into the one or more second apertures 128 fixes the second fastener 134 and the ventilation panel 110 to the straps 116. For example, the one or more second apertures 128 may each include a first portion 142 and a second portion 144. The second portion 144 may extend from the front side 122 of the strap 116 and terminate at the first portion 142. The first portion 142 may extend from the rear side 124 of the strap and may have a substantially constant inner diameter. The second portion 144 may be tapered so that the one or more second fasteners 134 is retained within the second aperture 128 after insertion. Each of the one or more first apertures 126 may spaced apart from a respective sidewall 138 by a first width $W_1$ and each of the one or more second apertures 128 may be spaced apart from a respective sidewall 138 by a second width W2 that is greater than the first width $W_1$.

The first width $W_1$ and the second width W2 are illustrated as being measured to the center lines of the one or more first apertures 126 and the one or more second apertures 128. However, it should be understood the widths may be measured from any position within each aperture. For example, the widths may be measured from the closest or farthest edges of the respective apertures to the respective sidewall 138.

To install the insulative member 114 and the ventilation panel 110 to the rear wall 104 of the refrigerator, the insulative member 114 may be inserted between the first strap 116a and the second strap 116b such that the insulative member 114 is fixed therebetween. The first and second straps 116a, 116b may be fixed (e.g., fastened to the rear wall 104) such that the straps 116 and the insulative member 114 lie against the rear wall 104. The ventilation panel 110 may be pressed towards the strap 116 and the insulative member 114 so that the ventilation panel 110 is fixed to the strap 116.

Figure 1:
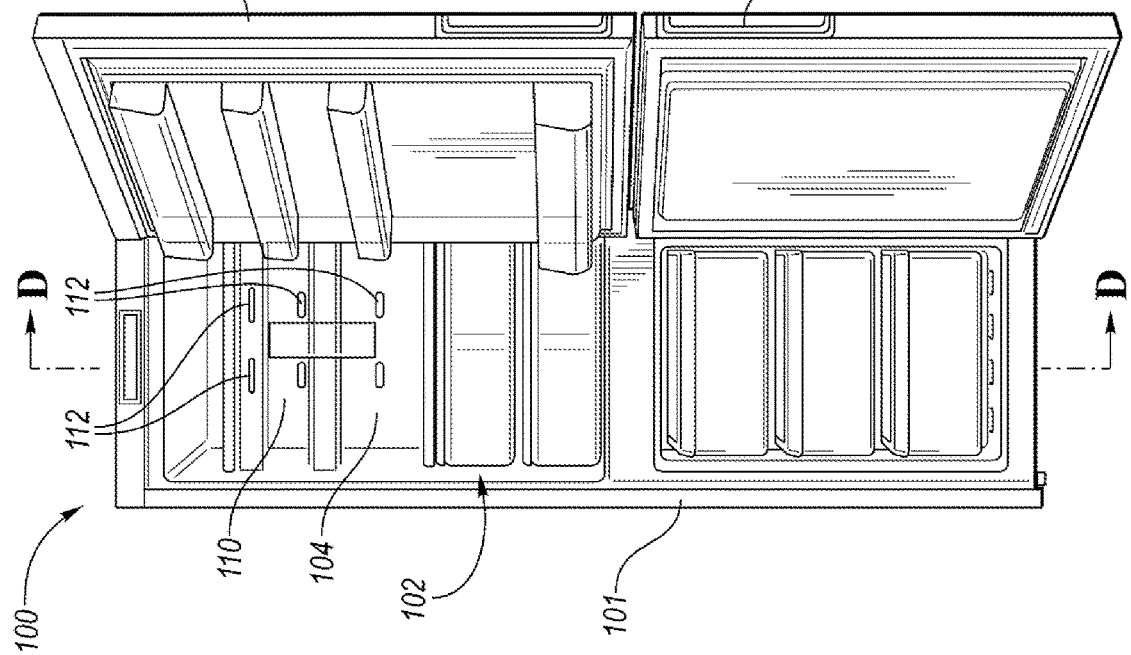
FIG. 1 is a front view of an exemplary refrigerator.

FIG. 1 illustrates a front view of the refrigerator 100 in an assembled state. The ventilation panel 110 lies along portions of the rear wall 104 and covers the strap 116 and insulative member 114. The refrigerator 100 illustrated includes an upper refrigerator section and a lower freezer section. The refrigerator 100 illustrated also includes shelving and storage bins. However, the present disclosure applies to other configurations of refrigerators.

FIG. 2 illustrates a portion of the refrigerator 100 with the shelving, storage bins, and the ventilation panel 110 removed. The insulative member 114 may be elongated having a length that is greater than the width and may be disposed in the recessed portion 118 of the rear wall 104. As an example, the insulative member 114 may be formed of a cellular foam material such as a closed cell foam (e.g., expanded polystyrene). One or more apertures may form vents 146 in the insulative member 114 and the vents 146 may be substantially aligned with the vents 112 of the ventilation panel 110.

Figure 2A:
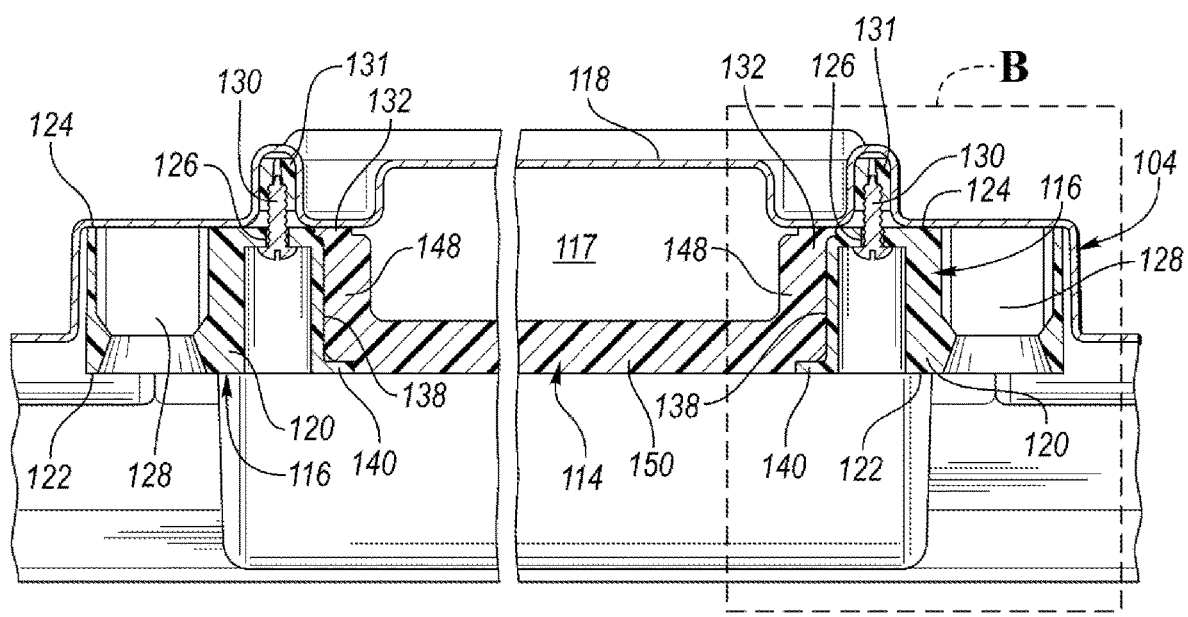
FIG. 2A is a partial cross-sectional view taken along line A-A in FIG. 2.

FIG. 2A illustrates a cross-sectional view of the insulative member 114, straps 116, and rear wall 104 taken along the line A-A in FIG. 2. The insulative member 114 may have a substantially U-shaped cross section including two legs 148 extending from a medial portion 150. The medial portion 150 and portions of the recessed portion 118 of the rear wall 104 may define the duct 117.

Figure 2B:
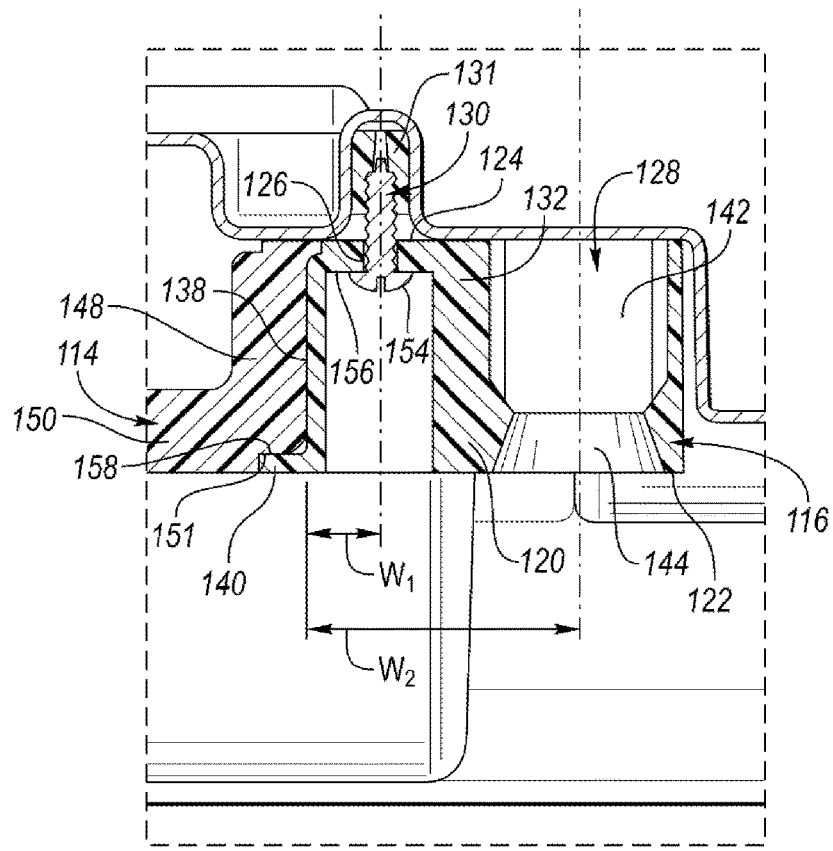
FIG. 2B is a magnified view of the area B in FIG. 2A.

FIG. 2B illustrates a detailed view of a portion of the insulative member 114, strap 116, and rear wall 104 encompassing the area B from FIG. 2A. Each of the legs 148 of the insulative member 114 and the medial portion 150 may define a recess portion 151 that may lie against the flange 140 of one of the straps 116 such that each strap 116 and the rear wall 104 sandwich one of the legs 148 of the insulative member 114. When the ventilation panel 110 is assembled to the straps 116, the flanges 140 may be sandwiched between the insulative member 114 (or more specifically the leg 148 of the insulative member 114) and the ventilation panel 110.

Each first fastener 130 may include a head 154 that may engage a clamping surface 156 on a respective strap 116. As the first fastener 130 is tightened, the flange 140 may engage and bias or clamp the leg 148 towards the rear wall 104. More specifically a clamping surface 158 on each flange 140 may engage a respective recess portion 151 on a respective leg 148 of the insulative member 114. This may provide a clamping force between the insulative member 114 and the rear wall 104 resulting in an insulative seal between the insulative member 114 and the rear wall 104. As another example, this may prevent the insulation member 114 from protruding into the internal chamber 102 so that the ventilation panel 110 (FIG. 3A) may be flush to the insulative member 114, or the rear wall 104, or both.

Figure 3:
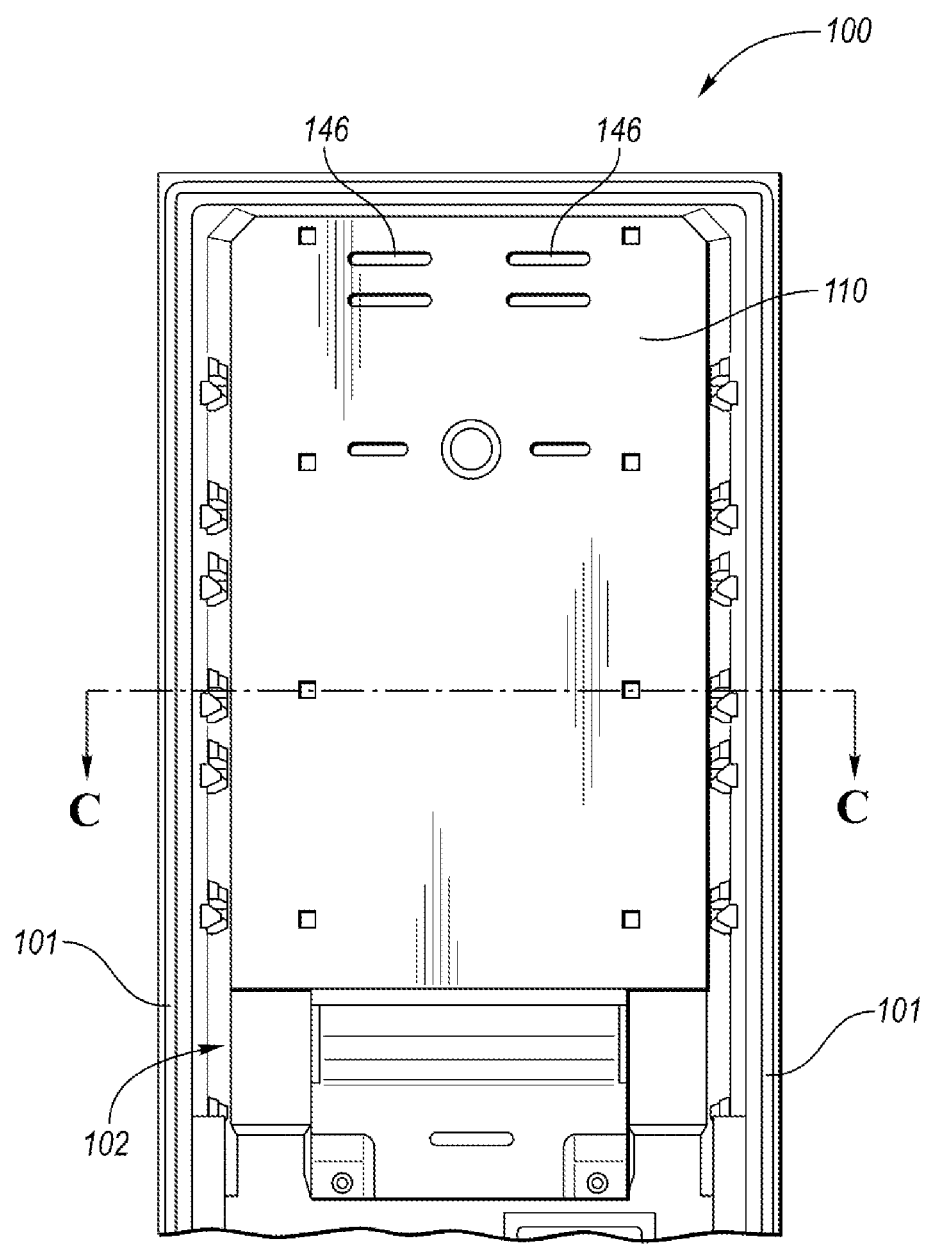
FIG. 3 illustrates a front view of a portion of the refrigerator including a vent panel with the shelving and storage bins removed.
Figure 3A:
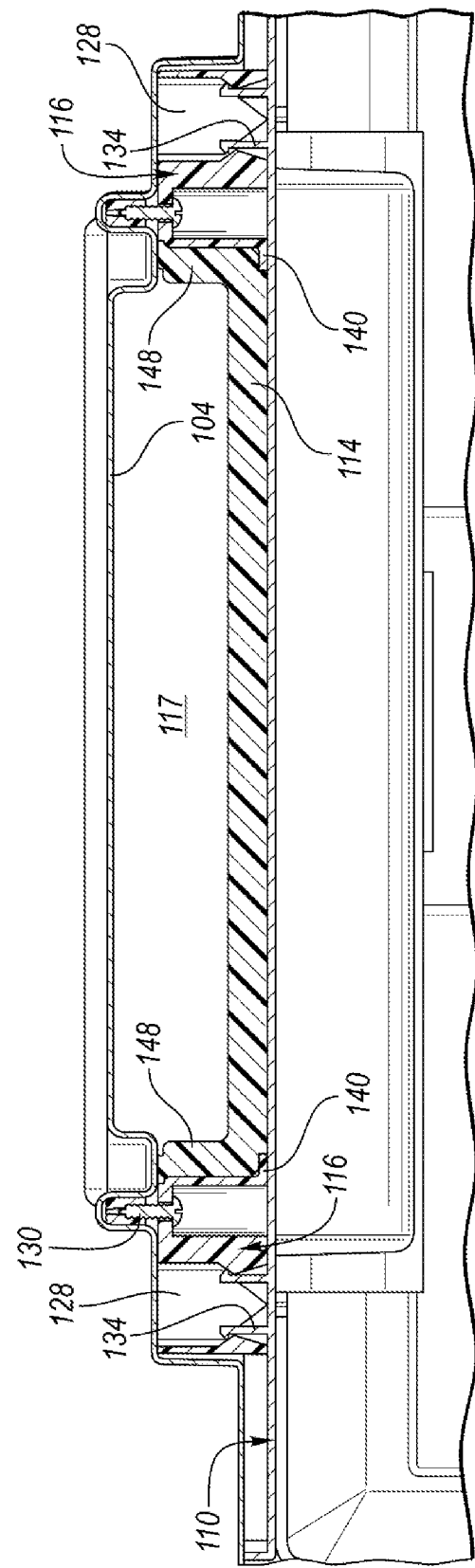
FIG. 3A is a cross-sectional view taken along line C-C in FIG. 3.
Figure 4:
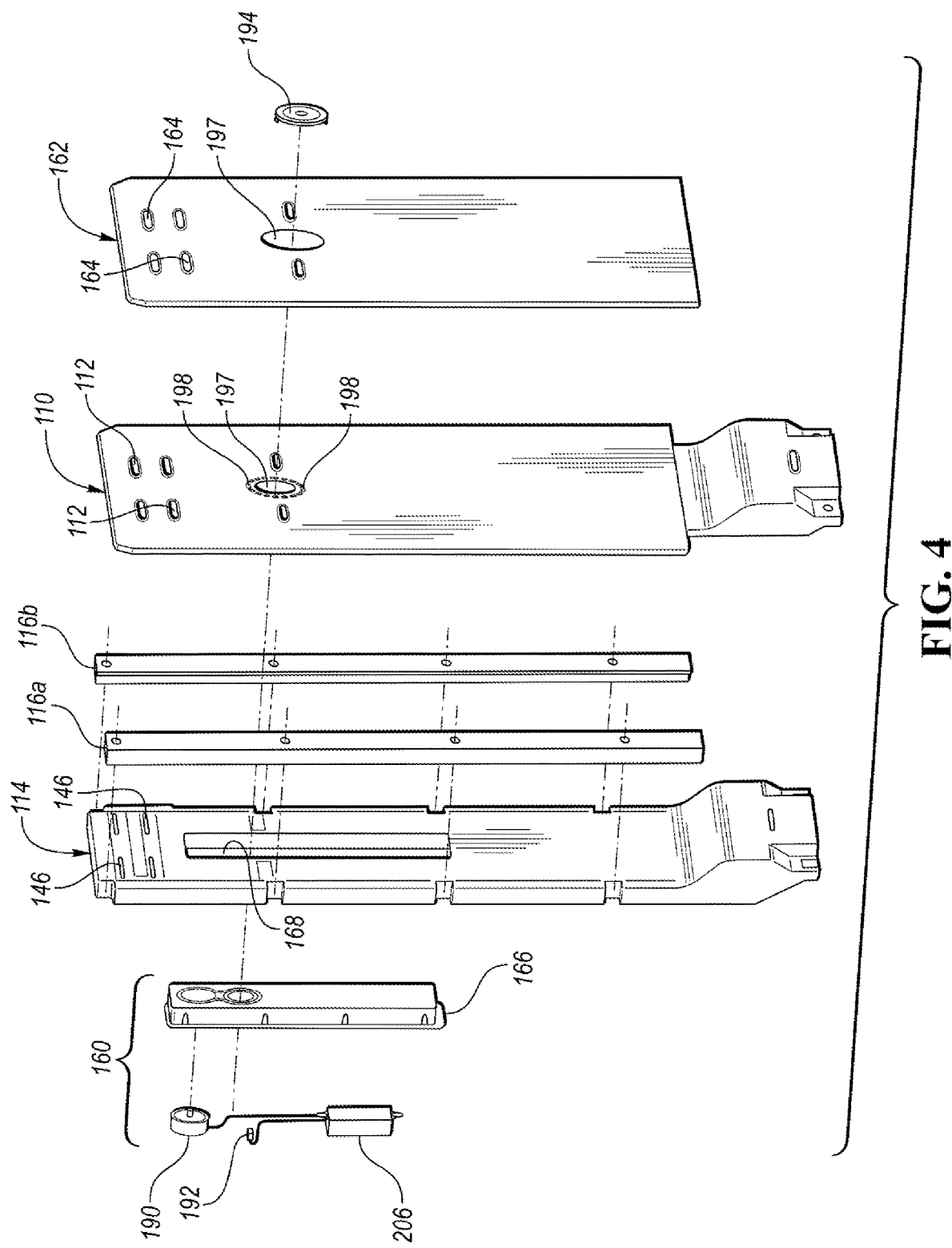
FIG. 4 is an exploded view of internal components of the refrigerator including an insulative member, a mounting system for the insulative member, and an ozone generator assembly.
Figure 5:
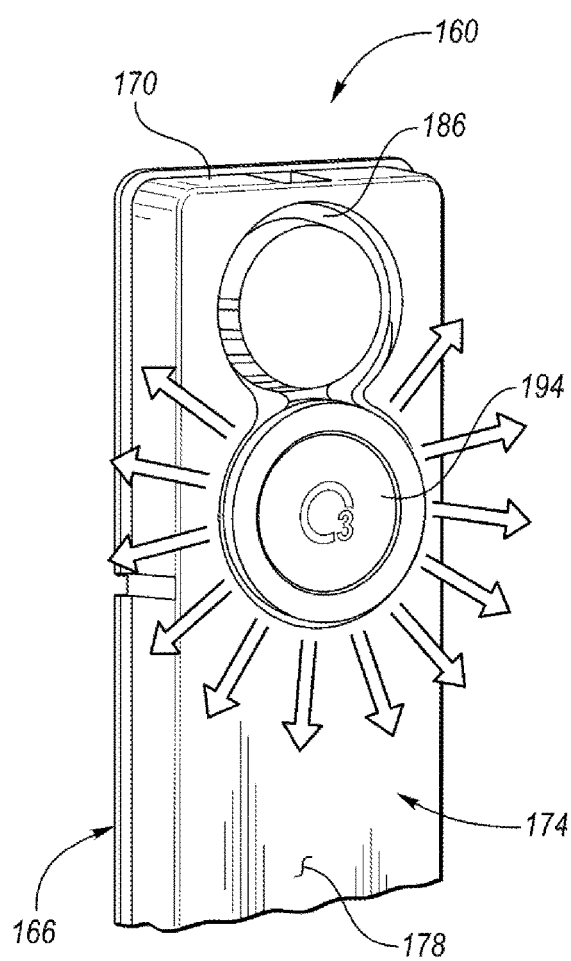
FIG. 5 is a partial isometric front view of an ozone generator assembly.
Figure 6:
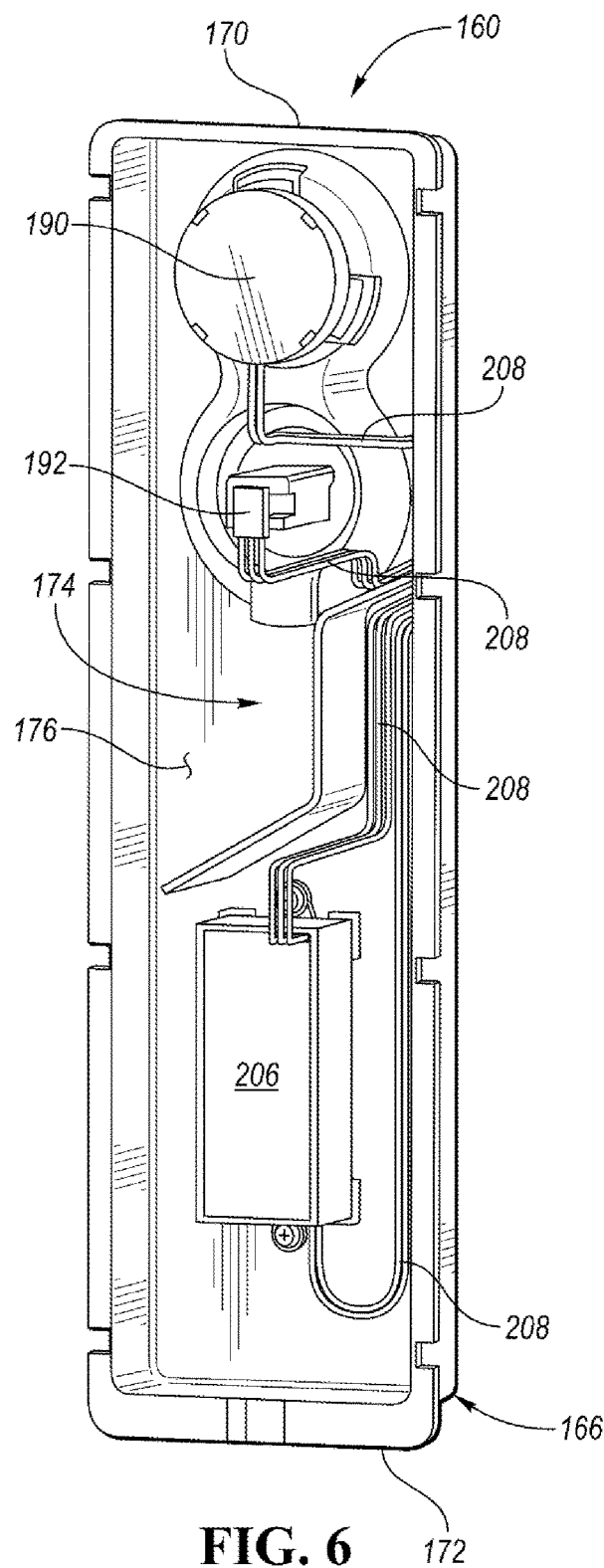
FIG. 6 is an isometric rear view of the ozone generator assembly.
Figure 7:
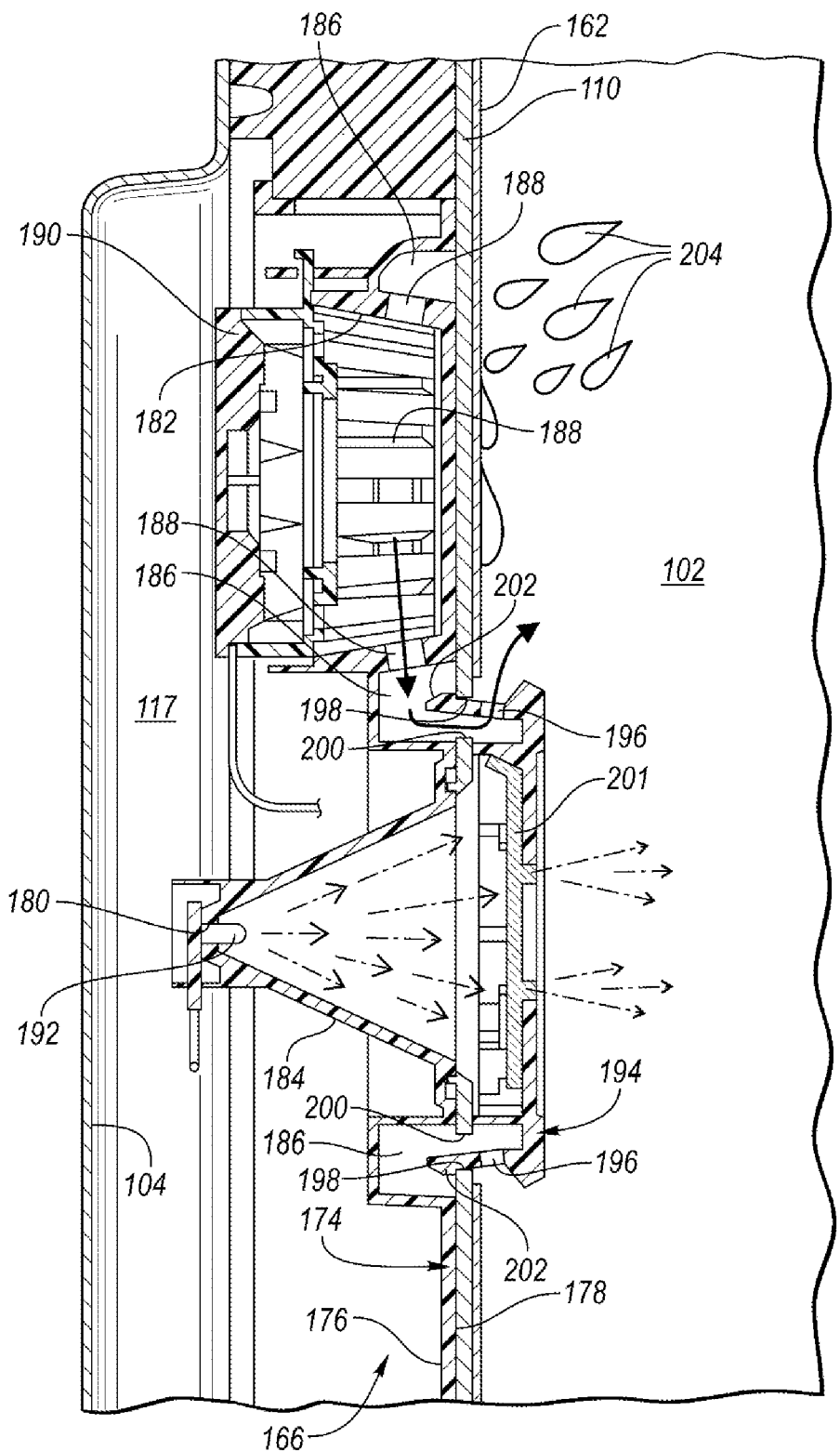
FIG. 7 is a partial cross-sectional view taken along line D-D in FIG. 1.

FIG. 3 illustrates a front view of a portion of the refrigerator 100 including the ventilation panel 110 with the shelving and storage bins removed. FIG. 3A illustrates a cross-sectional view taken along the line C-C in FIG. 3. The one or more second fasteners 134 are shown to protrude from the ventilation panel 110. However, it should be understood that the fasteners 134 may be components that are separate from the ventilation panel 110. Each of the one or more second fasteners 134 are also show to and to engage one of the one or more second apertures 128 to secure the ventilation panel 110 to the straps 116. Utilizing a press-fit fastener, such as the second one or more second fasteners 134, obviates excess assembly time required for a threaded fastener as well as the additional assembly time to insert a cover or plug to conceal the heads of threaded fasteners. The straps 116 and any associated feature or component (e.g., fasteners 130 and 134) may collectively be referred to as a fixation system for use in the refrigerator 100 that is configured to secure the insulative member 114 to the rear wall 104 and to secure the ventilation panel 110 to the insulative member 114.

Referring now to FIG. 4-9, some of the internal components of the refrigerator 100 including the insulative member 114, the mounting system for the insulative member (e.g., the fixation system that collectively includes the straps 116 and other components mentioned above), and an ozone generator assembly 160, are illustrated. The refrigerator 100 may also include a second ventilation or flow panel 162 that is disposed over the ventilation panel 110 to provide an aesthetic look. For example, the second ventilation panel 162 may be made from a finished metallic material such as aluminum or stainless steel. One or more apertures may form vents 164 in the second ventilation panel 162. The vents 164 in the second ventilation panel 162 may be substantially aligned with the vents 112 in the ventilation panel 110 and the vents 146 in the insulative member 114 such that the aligned vents may vent air from the internal chamber 102 to the exterior of the refrigerator 100 via the duct 117.

The ozone generator assembly 160 includes a housing 166. The insulative member 114 may define an aperture 168. The housing 166 may be disposed within the aperture 168. The housing 166 may include a top end 170, a bottom end 172, and a wall 174 extending between the top end 170 and the bottom end 172. The wall 174 includes an interior-facing surface 176 and an exterior-facing surface 178 that is opposite the interior-facing surface 176. The interior-facing surface 176 faces toward the duct 117. The exterior-facing surface 178 faces toward the internal chamber 102 of refrigerator 100. The ventilation panel 110 and the second ventilation panel 162 may be sandwiched between exterior-facing surface 178 of the wall 174 of the housing 166 and the internal chamber 102 of refrigerator 100. The exterior-facing surface 178 may be referred to as a frontside of the wall 174 and the interior-facing surface 176 may be referred to as a backside of the wall 174.

The wall 174 (or more specifically the interior-facing surface 176 of the wall 174) defines an aperture 180 and a pocket or receptacle 182 that is disposed above the aperture 180. The aperture 180 may be configured to receive a light source and may be defined within a recessed portion of the wall 174 that forms a light fixture 184. The exterior-facing surface 178 may have a recessed portion that extends inward from the exterior-facing surface 178 defining a trough 186. The recessed portion that extends inward from the exterior-facing surface 178 and/or the trough 186 may define the receptacle 182 on the interior-facing surface 176. The trough 186 may extend circumferentially about at least a portion of the receptacle 182 and about at least a portion of the light fixture 184. The housing 166 defines a first number of vents 188 that establish fluid communication between the receptacle 182 and the trough 186.

An ozone generator 190 is at least partially disposed in the receptacle 182. The ozone generator 190 is configured to supply ozonated fluid to the trough 186 via the receptacle 182 and the first number of vents 188. The ozonated fluid may be utilized to sanitize the internal chamber 102 of the refrigerator 100 or anything disposed within the internal chamber 102 of the refrigerator 100. A light 192 is secured to the wall 174 of housing 166. More specifically, the light 192 is secured to the light fixture 184 within the aperture 180. The light 192 and the light fixture 184 may be disposed between the bottom end 172 of the housing 166 and the ozone generator 190 (i.e., 192 the light fixture 184 may be disposed below the ozone generator 190). The light 192 may be a sanitizing light that is also utilized to sanitize the internal chamber 102 of the refrigerator 100 or anything disposed within the internal chamber 102 of the refrigerator 100. The light 192 may be any type of light including a light emitting diode (LED).

The light 192 may include a cover 194 that is disposed over the exterior-facing surface 178 (or more specifically, the light fixture 184) of the wall 174 of the housing 166. The cover 194 overlaps at least a portion of the trough 186. The cover 194 may define a second number of vents 196 that are configured to receive the ozonated fluid from the first number of vents 188 via the trough 186. The second number of vents 196 may be defined circumferentially around a radial outer surface of the cover 194. The second number of vents 196 may then provide the ozonated fluid to an interior portion (i.e., the internal chamber 102) of the refrigerator 100. The ventilation panel 110 and the second ventilation panel 162 may each define aligned apertures 197 that are disposed between the cover 194 and the light fixture 184 to allow light to travel from the light fixture 184 via the light 192 to the cover 194. The cover may include a front plate 199 and rear plate 201. The front plate may define an orifice 203 that is in the shape of symbol that is indicative of ozonated fluid. The rear plate 201 may be translucent and may be configured to direct the light from the light 192 to the orifice 203.

The ventilation panel 110 and the second ventilation panel 162 may be disposed over the trough 186 and at least a portion of the exterior-facing surface 178 of the wall 174. The ventilation panel 110 defines at least one slot 198. The slots of the at least one slot 198 may be disposed circumferentially about the aligned aperture 197 defined by the ventilation panel 110. The aligned aperture 197 defined by the second ventilation panel 162 may larger than the aligned aperture 197 defined by the ventilation panel 110 such that the aligned aperture 197 defined by the second ventilation panel 162 overlaps both the aligned aperture 197 defined by the ventilation panel 110 and the slots of the at least one slot 198. The at least one slot 198 may alternatively be referred to as at least one aperture or a plurality of apertures. The at least one slot 198 is in fluid communication with and is aligned with the trough 186. More specifically, an inner periphery 200 of the at least one slot 198 is in fluid communication with and is aligned with the trough 186. The at least one slot 198 is configured to receive ozonated fluid from the ozone generator 190 via the trough 186, first number of vents 188, and receptacle 182. The second number of vents 196 are in fluid communication with the at least one slot 198 and are configured to vent the ozonated fluid from the at least one slot 198 to an interior portion (i.e., the internal chamber 102) of the refrigerator 100.

The ozonated fluid is routed through a channel that collectively includes the receptacle 182, the first number of vents 188, the trough 186, the at least one slot 198, and the second number of vents 196. The cover 194 for the light 192 may include protrusions or legs 202 that extend into the slots of the at least one slot 198. The legs 202 may engage the ventilation panel 110 proximate the slots of the at least one slot 198 to secure the position of the cover 194. One or more of the legs 202 may define at least one of the second number of vents 196. This collective channel that includes the receptacle 182, the first number of vents 188, the trough 186, the at least one slot 198, and the second number of vents 196 routes the ozonated fluid downward from the ozone generator 190. The ozone generator 190, the receptacle 182, the first number of vents 188, and at least a portion of the trough 186 are then covered by the ventilation panel 110 (i.e., the ventilation panel 110 overlays the exterior-facing surface 178 of the wall 174). Routing the ozonated fluid downward and covering the ozone generator 190, the receptacle 182, the first number of vents 188, and at least a portion of the trough 186 prevents an ingress of fluid 204, such as water, into the ozone generator 190, which could result in damage to the ozone generator 190.

The ozone generator 190 and the light 192 may each be connected to an electrical box or electrical block 206 via wires 208. The electrical block 206 may include a controller or may be connected to a controller that is configured to operate the ozone generator 190 and the light 192. The controller may be configured to, responsive to receiving first signals from the ozone generator 190 that are indicative of a first operating condition, provide second signals to the light 192 to display an indicator, wherein the indicator is configured to communicate the first operating condition to a user. The operating condition may at least partially be based on a quantity of ozonated fluid being supplied to the internal chamber 102 of the refrigerator 100 via the channel that collectively includes the receptacle 182, the first number of vents 188, the trough 186, the at least one slot 198, and the second number of vents 196.

More specifically, the controller may be configured to receive signals from the ozone generator 190 that is indicative of the ozone generator 190 being off, the ozone generator 190 being on, or a quantity of ozonated fluid being supplied to the internal chamber 102 of the refrigerator 100, each being a different operating condition. The controller may then send signal to the light 192 to illuminate the light 192, to turn off the light 192, dim the light 192, brighten the light, or strobe the light 192 to correspond to a specific operating condition. For example, the light 192 being off may correspond to the ozone generator 190 being off, the light 192 being on may correspond to the ozone generator 190 being on, an increase in the brightness of the light 192 may correspond to an increase in the quantity of ozonated fluid being supplied to the internal chamber 102, a decrease in the brightness of the light 192 may correspond to a decrease in the quantity of ozonated fluid being supplied to the internal chamber 102, etc.

The controller may be part of a larger control system and may be controlled by various other controllers throughout the refrigerator 100. It should therefore be understood that the controller and one or more other controllers can collectively be referred to as a "controller" that controls various functions or components of the refrigerator 100 in response to signals from various sensors to control the various functions or components of the refrigerator. The controller may include a microprocessor or central processing unit (CPU) in communication with various types of computer readable storage devices or media. Computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the CPU is powered down. Computer-readable storage devices or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller in controlling the refrigerator 100.

It should be understood that the designations of first, second, third, fourth, etc. for any component, state, or condition described herein may be rearranged in the claims so that they are in chronological order with respect to the claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A refrigerator comprising:
   a rear wall;
   a first strap and a second strap each fixed to the rear wall;
   an insulative member defining a first aperture and extending between the first strap and the second strap;
   a housing disposed in the first aperture, the housing including a top end, a bottom end, and a wall extending therebetween, a frontside of the wall having a recessed portion that defines a receptacle on a backside of the wall, a trough on the frontside of the wall, and a first number of vents, wherein the first number of vents establish fluid communication between the receptacle and the trough;
   an ozone generator disposed in the receptacle;
   a first ventilation panel disposed over the trough and at least a portion of the frontside of the wall, the first ventilation panel being fixed to the insulative member and defining at least one slot, wherein the at least one slot is in fluid communication with the trough and is configured to receive ozonated fluid from the ozone generator via the trough, first number of vents, and receptacle; and
   a light fixed to the wall and disposed between the bottom end and the ozone generator, the light including a cover that overlaps at least a portion of the trough and defines a second number of vents, wherein the second number of vents are in fluid communication with the at least one slot and are configured to vent the ozonated fluid from the at least one slot to the an interior portion of the refrigerator.

2. The refrigerator of claim 1, wherein an inner periphery of the at least one slot is aligned with the trough.

3. The refrigerator of claim 1, wherein the trough extends circumferentially about at least a portion of the receptacle.

4. The refrigerator of claim 1, wherein the first and second straps include flanges that engage the insulative member to secure the insulative member to the rear wall.

5. The refrigerator of claim 1 further comprising a second ventilation panel disposed over the first ventilation panel, wherein the second ventilation panel defines a third number of vents each configured to facilitate an exchange of air between the interior portion of the refrigerator and a rear portion of the refrigerator.

6. The refrigerator of claim 1, wherein the cover includes legs that extend into the at least one slot.

7. The refrigerator of claim 6, wherein the trough, the plurality of apertures, and the second number of vents form a channel configured to communicate the ozonated fluid from the first number of vents to the interior portion of the refrigerator.

8. The refrigerator of claim 1, wherein the at least one of the legs defines at least one of the second number of vents.

9. An ozone generator assembly for use in a refrigerator, the ozone generator assembly comprising:
   a housing including a top end, a bottom end, and a wall extending therebetween, the wall including an interior-facing surface defining a first aperture and a receptacle disposed above the first aperture, the wall including an exterior-facing surface that is opposite the interior-facing surface, the exterior-facing surface defining a trough that extends inward from the exterior-facing surface and extends circumferentially about at least a portion of the receptacle, the housing defining a first number of vents that establish fluid communication between the receptacle and the trough;
   an ozone generator at least partially disposed in the receptacle and configured to supply ozonated fluid to the trough via the receptacle and the first number of vents; and
   a light secured to the housing and disposed in the first aperture, the light including a cover disposed over the exterior-facing surface of the wall, the cover defining a second number of vents configured to receive the ozonated fluid from the first number of vents via the trough and provide the ozonated fluid to an interior portion of the refrigerator.

10. The ozone generator assembly of claim 9, further comprising:
    a controller operatively connected to the light and the ozone generator, the controller configured to, responsive to receiving first signals from the ozone generator indicative of a first operating condition, provide second signals to the light to display an indicator, wherein the indicator is configured to communicate the first operating condition to a user.

11. The ozone generator assembly of claim 10, wherein the operating condition is at least partially based on a quantity of ozonated fluid supplied to the first number of vents.

12. The ozone generator assembly of claim 9, further comprising a ventilation panel disposed on the exterior-facing surface of the housing, wherein the ventilation panel defines a number of third vents each configured to facilitate an exchange of air between the interior portion of the refrigerator and a rear portion of the refrigerator.

13. The ozone generator assembly of claim 12, wherein the ventilation panel defines a plurality of apertures and the cover includes legs that extend into the plurality of apertures.

14. The ozone generator assembly of claim 13, wherein the trough, the plurality of apertures, and the second number of vents form a channel configured to communicate the ozonated fluid from the first number of vents to the interior portion of the refrigerator.

15. The ozone generator assembly of claim 13, wherein at least one of the legs defines at least one of the second number of vents.

* * * * *